US008563315B2

(12) United States Patent
Zey et al.

(10) Patent No.: US 8,563,315 B2
(45) Date of Patent: Oct. 22, 2013

(54) CALIBRATION SUBSTANCES FOR ATMOSPHERIC PRESSURE ION SOURCES

(75) Inventors: Thomas Zey, Oyten (DE); Jan Willmann, Ritterhude (DE)

(73) Assignee: Bruker Daltonik GmbH, Bremen (DE)

( * ) Notice: Subject to any disclaimer, the term of this patent is extended or adjusted under 35 U.S.C. 154(b) by 64 days.

(21) Appl. No.: 12/727,829

(22) Filed: Mar. 19, 2010

(65) Prior Publication Data

US 2010/0237230 A1 Sep. 23, 2010

(30) Foreign Application Priority Data

Mar. 19, 2009 (DE) ........................ 10 2009 013 914

(51) Int. Cl.
*B01D 59/44* (2006.01)
*H01J 49/00* (2006.01)
*G01N 33/92* (2006.01)

(52) U.S. Cl.
USPC .................... 436/8; 436/13; 436/71; 436/173

(58) Field of Classification Search
USPC .......................................... 436/8, 13, 71, 173
See application file for complete search history.

(56) References Cited

U.S. PATENT DOCUMENTS 3,678,104 A * 7/1972 Vesely et al. .................. 562/475
4,224,031 A * 9/1980 Mee et al. ..................... 436/173
4,665,225 A * 5/1987 Frihart .......................... 562/507
5,665,602 A * 9/1997 Caviezel ......................... 436/71
5,670,345 A * 9/1997 Srivastava et al. .............. 435/75
5,872,357 A 2/1999 Flanagan
6,489,135 B1 * 12/2002 Parrott ............................ 435/21
6,558,902 B1 5/2003 Hillenkamp
2003/0068653 A1 * 4/2003 Parrott ........................... 435/7.1
2003/0162833 A1 * 8/2003 Roe ............................... 514/547
2003/0187226 A1 * 10/2003 Goodey et al. ................ 530/362

(Continued)

FOREIGN PATENT DOCUMENTS

EP 0655769 5/1995

OTHER PUBLICATIONS

Aldrich Chemical Catalog 1988, pp. 1610-1612.*

(Continued)

*Primary Examiner* — Arlen Soderquist
(74) *Attorney, Agent, or Firm* — O'Shea Getz P.C.

(57) ABSTRACT

A Mixture of substances is provided for precise calibration of the mass scale of mass spectrometers equipped with ion sources that operate at atmospheric pressure (AP) with ionization of the analyte molecules, for example by APCI (chemical ionization), or by APPI (photoionization), often at high temperatures of up to 470° C. Out of physical reasons, the mass scale of any time-of-flight mass spectrometer deviates in the lower mass range from the theoretical relation between charge-related mass m/z and flight time t. A closely spaced arrangement of low mass calibration reference points is necessary if high mass accuracy is to be achieved for substances of low molecular weight. APCI and APPI sources are increasingly used in time-of-flight mass spectrometers with orthogonal ion injection (OTOF MS) for the detection of non-polar and weakly polar compounds, in particular, for analyte molecules with relatively low molecular weights. Calibration substances in solutions that are easily handled, nontoxic, stable at the high temperatures involved, will accept both positive and negative ionization, and supply enough reference points for calibration in the mass range up to 500 daltons. Mixtures of saturated fatty acids dissolved in toluene may be used. For photoionization, also mixtures of phenyl and naphthyl fatty acids.

14 Claims, 4 Drawing Sheets

(56) References Cited

U.S. PATENT DOCUMENTS

| | | | | |
|---|---|---|---|---|
| 2004/0129876 | A1* | 7/2004 | Franzen | 250/288 |
| 2005/0230457 | A1* | 10/2005 | Kay et al. | 228/260 |
| 2006/0004099 | A1* | 1/2006 | Roe | 514/558 |
| 2006/0117401 | A1* | 6/2006 | Schmitz et al. | 800/278 |
| 2006/0137042 | A1* | 6/2006 | Plesch et al. | 800/288 |
| 2006/0218990 | A1* | 10/2006 | Kawana | 73/23.37 |
| 2007/0202073 | A1* | 8/2007 | Fenyvesi et al. | 424/70.31 |
| 2008/0004342 | A1* | 1/2008 | Zaloga et al. | 514/506 |
| 2008/0234945 | A1* | 9/2008 | Walk et al. | 702/19 |
| 2008/0308724 | A1 | 12/2008 | Brekenfeld | |
| 2010/0163720 | A1* | 7/2010 | Bethan et al. | 250/282 |
| 2010/0317734 | A1* | 12/2010 | Folan et al. | 514/558 |
| 2011/0207819 | A1* | 8/2011 | Boll | 514/547 |

OTHER PUBLICATIONS

Eichelberger. J. W. et al, Analytical Chemistry 1975, 47, 995-1000.*
de Jong, C. et al, Journal of High Resolution Chromatography 1990, 13, 94-98.*
Lin, H.-Y. et al, Journal of Mass Spectrometry 1994, 30, 381-383.*
Eckers. C, et al, Analytical Chemistry 2000, 72, 3683-3688.*
Wallick, R. H. et al, Analytical Chemistry 1969, 41, 388-390.*
Gilliam, J. M. et al, Analytical Chemistry 1984, 56, 2285-2288.*
Ballantine, J. A. et al, Organic Mass Spectrometry 1987, 22, 316-318.*
Schmidt, C. E. et al, Analytical Chemistry 1987, 59, 2027-2033.*
Heeremans, C. E. M. et al, Organic Mass Spectrometry 1989, 24, 109-112.*
Tinke, A. P. et al, Rapid Communications in Mass Spectrometry 1991, 5, 188-191.*
Saar, J. et al, Organic Mass Spectrometry 1991, 26, 660-663.*
Cody, R. B. et al, Analytical Chemistry 1992, 64, 1561-1570.*
Brinded, K. L. et al, Rapid Communications in Mass Spectrometry 1993, 7, 1059-1061.*
Moini, M. et al, Journal of the American Society for Mass Spectrometry, 1998, 9, 977-980.*
Storm, T. et al, analytical Chemistry 2001, 73, 589-595.*
Garofolo, F., "LC-MS Instrument Calibration" in Analytical Method Validation and Instrument Performance Verification, Chow, C. et al, editor, 2004, John Wiley & Sons, Inc, pp. 197-220.*
Stout et al. "Tuning and Calibration in Thermospray Liquid Chromatography/Mass Spectrometry Using Perfluorinated Alkyl Acids and their Ammonium Salts", Organic Mass Spectrometry, vol. 25, 1990, pp. 187-190.

* cited by examiner

CALIBRATION SUBSTANCES FOR ATMOSPHERIC PRESSURE ION SOURCES

PRIORITY INFORMATION

This patent application claims priority from German patent application 10 2009 013 914.1 filed on Mar. 19, 2009, which is hereby incorporated by reference.

FIELD OF THE INVENTION

The invention relates to mass spectrometry, and in particular to mixtures of substances for calibration of a mass scale of mass spectrometer equipped with an ion source that operates at atmospheric pressure (AP) with ionization of the analyte molecules.

BACKGROUND OF THE INVENTION

Time-of-flight mass spectrometers with orthogonal ion injection (OTOF-MS) are commonly operated with electrospray ion sources (ESI), but increasingly they are operated also with ion sources for other types of ionization, such as chemical ionization and photoionization. Because these ion sources operate at atmospheric pressure, they have become known as atmospheric pressure chemical ionization (APCI) and atmospheric pressure photoionization (APPI) sources. APCI and APPI extend the scope of analyzable substances to those that are less strongly polar. Electrospray ion sources are commonly coupled with liquid chromatographs such as high performance liquid chromatographs (HPLC). APCI and APPI ion sources, however, also permit the connection with gas chromatographs (GC), since the substances separated by GC can also be ionized by APCI and APPI. This possibility extends the application of OTOF mass spectrometers, but requires accurate mass determination in the lower mass range.

Accurate mass determination is required because these ion sources deliver only molecular ions, not the signal-rich mass spectra delivered by electron bombardment ion sources (EI) usually used in GC-MS work. In prior art GC-MS, substances were identified by spectrum comparisons; libraries with hundreds of thousands of EI mass spectra are available for this purpose. However, the molecular ions delivered by APCI and APPI ion sources in OTOF-MS instruments facilitate calculating the molecular formula of the substance under investigation, if the mass accuracy is good enough. The molecular formula is first step for the identification of a substance; the measurement of fragment ion spectra of selected molecular ions may then complete the identification.

APCI and APPI ion sources regularly use high temperatures (e.g., 200° C.-470° C.), in order that the solvate sheaths are removed from the analyte molecules, without which ionization could not take place at all. The heat is supplied via the spray gas, sometimes also known as the nebulization gas. If the analyte substances are not supplied by gas chromatographs, and if the analyte solution is supplied in liquid form, the hot spray gas also has to nebulize the analyte solution and to evaporate the droplets. This method of operating the APCI and APPI ion sources can also be transferred to light analyte substances, particularly those that are either weakly polar or non-polar; here too, the lower mass range requires special measures to preserve mass precision and accuracy.

An APCI ion source uses a similar housing to that of an electrospray ion source. The spray device is operated without the spray voltage; only the spray gas is used for the nebulizing and evaporation of the solution containing analyte molecules.

In order to evaporate the solvent and to remove the solvate sheath from the analyte molecules, the spray or nebulizer gas is strongly heated in a heating block to temperatures of up to 470° C. The chemical ionization is produced by reactant ions that are formed, in a chain of reactions, from primary ions of molecules of the ambient gas, usually air. These primary ions are generated in a corona discharge at the tip of a suitable metal needle, to which a few thousand volts are applied. The primary ions, usually of nitrogen, react with the water molecules in the moisture contained in the ambient gas, to form complex molecules of the form $N_m(H_2O)_nH^+$ or $N_m(H_2O)_nOH^-$; these are capable of causing protonation or, in a negative operating mode, deprotonation, of the analyte molecules, so causing the chemical ionization.

An APPI ion source is similar to an APCI ion source, but rather than employing a corona discharge, radiation from a UV lamp is generally used for the ionization. If a UV laser is employed, we speak of atmospheric pressure laser ionization (APLI), although this is also a type of photoionization. Only the substance molecules that can absorb the UV radiation can be directly ionized in this way; these are primarily aromatic substances. By adding an aromatic mediator substance, the mediator substance can be ionized, and its ions can then serve as reactant ions to chemically ionize many types of analyte molecule. So APPI in many cases operates as indirect APCI.

Both types of ionization can advantageously be coupled with liquid chromatography, and are used when particular substance groups of low polarity cannot be ionized by electrospraying. In contrast to biopolymers such as proteins, which can easily be ionized by electrospraying, ionization is often not successful for other kinds of organic substance; and these frequently have relatively low molecular weights.

APCI and APPI can also be coupled with gas chromatography. For this purpose the gas chromatographic separating capillary is brought into the ionization chamber of the electrospray ion source, where it releases the separated analyte substances into the ionization chamber. Coupling the gas chromatography with time-of-flight mass spectrometers of high mass accuracy provides new possibilities for quickly establishing correct molecular formulas for the analyte molecules. When gas chromatography is coupled with ion trap or quadrupole mass spectrometers via electron impact ion sources, which has been the usual method up to now, the relatively low mass accuracy only permits the identification of substances through spectral comparisons; this fails in the case of unknown substances, for instance in the analysis of unknown natural products.

Coupling an OTOF mass spectrometer with a gas chromatograph has also led to the development of APLI. Here, the photon density in the beam from a UV pulse laser is exploited to ionize aromatic substances directly by multiphoton processes. For this purpose, a rectangular cross-section of the laser light pulse beam is created directly in front of the GC capillary; with each laser light pulse, the width of the beam catches a proportion of the carrier gas as it flows out, so in combination with the laser light pulse frequency (usually 100 hertz), the whole of the GC eluate is recorded. In this way, the aromatic substances in the GC eluate are detected with great efficiency and high sensitivity. Through the additional use of mixtures of aromatic mediators such as benzene, toluene or similar substances, and of non-aromatic mediators such as chloroform, it is also possible to ionize many non-aromatic substances.

In the development of OTOF mass spectrometers, improvement of the mass accuracy is crucial for determining the masses of analyte ions. The aim is to achieve a mass accuracy of better than a millionth of the mass (one ppm).

Until now, however, attention has been paid to the mass range extending from about 500 up to a few thousand daltons because the main field of application of these mass spectrometers is the analysis of biopolymers, primarily proteins. Mass accuracy has until now been neglected in the range below 500 daltons; only recently has it been recognized that, in the lower mass range, the calibration curve differs significantly from the ideal calibration function, preventing accurate mass determination.

U.S. Published Patent Application 2008/0308724A1 discloses how deviations of the calibration curve from the theoretically expected curve in the lower mass range can be explained and described mathematically to a good approximation. The approximation allows the masses of the light ions in the lower mass range from about 100 to 500 daltons to be determined to within almost a millionth of the mass (1 ppm) if the coefficients of the mathematical equation for the calibration curve can be determined, by a sufficient number of reference points, precisely enough for a calibration. It is particularly advantageous if the reference points are separated from one another by the same mass difference.

In OTOF mass spectrometers, the ions from a section of a fine beam of ions are suddenly accelerated, perpendicular to their former flight direction, into the flight path, by an ion pulser. They are then reflected by a reflector at a slight angle onto the ion detector, where they are measured as a time-variable ion current that represents the time-of-flight spectrum. The accelerating voltages in the ion pulser, however, cannot be switched instantaneously, due to the capacitances of the lines and the pulser. In the best case of a critically damped switching, no overshooting and no oscillations occur and the voltage follows a transition curve whose time constant is a few nanoseconds long. Very light ions that can be accelerated quickly pass through the pulser before the full accelerating voltage has been reached. This results in deviations of the calibration curve $m/z=f(t)$ from the ideal curve $m/z=a\times t^2$, where m/z represents the mass m per elementary charge, t the time of flight, and is a constant. As mentioned, the best results for a relatively smooth calibration curve in the lower mass range are obtained by trying to achieve the critically damped case. If the ideal non-oscillating critically damped case is not achieved precisely, then either overshooting with subsequent oscillations or slow settling will occur, resulting in even larger, sometimes irregular, deviations. Unfortunately it is not always possible to maintain the non-oscillating conditions of critical damping because, for instance, aging processes in the electronic equipment or temperature changes cause the settings to drift.

The equations for best approximation given in U.S. Published Patent Application 2008/0308724A1 can be used to calibrate the mass spectrometer in the lower mass range. It is, however, also possible to perform accurate mass determinations without the knowledge of a mathematical approximation equation, by interpolating the masses between the stored reference points of the mass scale with an n-th order polynomial curve. Usually here, the time of flight t is first squared to achieve a rough linearization with reference to the mass values m, since, apart from the deviations considered above, the masses are proportional to the square $t^2$ of the flight time in a time-of-flight mass spectrometer. Here again it is advantageous if the reference points are separated from one another by the same mass difference.

Because the APCI, APPI and APLI ionization sources essentially deliver singly charged molecule ions, and no fragment ions, the generation of a mass spectrum with enough reference points of precisely known masses requires a calibration substance for each reference point; thus a mixture of calibration substances is needed.

Mixtures of substances that can be used to calibrate the mass scale in ESI-OTOF mass spectrometers are already known. Until now, however, these mixtures have always been intended for use in the high mass range between 500 and a few thousand daltons; there are only very few reference points in the lower mass range. For instance, in the work of S. J. Stout and A. R. daCunha, entitled "*Tuning and Calibration in Thermospray Liquid Chromatography/Mass Spectrometry Using Perfluorinated Alkyl Acids and Their Ammonium Salts*", which comes closest to the invention disclosed here because of the substances used, a mixture entirely of fluorinated fatty acids and their ammonium salts is described. However, this mixture only supplies two reference points in the mass range below 500 daltons. Furthermore, the salts decompose at the high temperatures that are applied here.

U.S. Pat. No. 5,872,357 discloses a mixture of various substituted triazatriphosphorine compounds. The mass spectrum of the mixture offers reference points with uniform mass spacings of either 300 or 600 daltons, whose masses are known precisely. Unfortunately, however, this mixture again only provides two reference points in the mass range up to 500, although already a non-related substance is added that provides a further reference point in the low mass range. This mixture of calibration substances is marketed with great commercial success, but for the reasons mentioned above can only be used for accurate mass determinations in the higher mass range from about 500 daltons up to around 3000 daltons. In this higher mass range, the calibration curve can be represented precisely by approximation equations whose curves are smooth and stiff, and require only a few reference points.

The requirements for a mixture of calibration substances for the lower mass range are as follows:

- the calibration substances should be thermally stable at temperatures up to 470° C.;
- they should supply at least five, and preferably ten, reference points below 500 daltons;
- the masses of the calibration substances should be as evenly spaced as possible;
- the calibration substances should be able to form both positive and negative ions;
- the calibration substances should be nontoxic;
- the calibration substances should be soluble in one another; and
- the solution of calibration substances should be capable of pulsed injection, and the signals from the calibration substances should rapidly diminish again, without a memory effect.

If these requirements are satisfied, then this mixture of substances can be used to develop an automated calibration method, which can be run regularly prior to, or even during, analytical procedures, and can therefore compensate for drifting of the mass scale.

SUMMARY OF THE INVENTION

A mixture of saturated fatty acids (alkane carboxylic acids) is provided, preferably dissolved in toluene, yielding sufficient reference masses in the range of 100 daltons to 500 daltons for calibrating the mass scale. A preferred mixture comprises a continuous series of the odd-numbered fatty acids extending from 5 C-atoms (valeric acid) up to 31 C-atoms, so providing 14 reference points. It is advantageous that these odd-numbered fatty acids are rarely found in nature where even-numbered fatty acids are highly preferred. The differences in mass amount to 28 daltons each. In the positive operating mode, the protonated molecule ions of the fatty acids are measured, while in the negative mode, the deprotonated molecule ions are used. In the positive mode, this provides reference points from 103 to 467 daltons, and in the negative mode from 101 to 465 daltons. The fatty acids are nontoxic. They are sufficiently stable, at least for a short period, in the temperature range up to 470° C. For APPI, the solvent toluene acts as a mediator with which, the fatty acids can be indirectly ionized, particularly when chloroform (trichloromethane) is also added as a second mediator.

For improved mass calibration spectra for APPI and APLI, a mixture of aromatically modified fatty acids (phenyl or naphthyl fatty acids) may be used. The aromatic groups enable the absorption of the UV radiation and therefore direct ionization.

These and other objects, features and advantages of the present invention will become more apparent in light of the following detailed description of preferred embodiments thereof, as illustrated in the accompanying drawings.

DETAILED DESCRIPTION OF THE INVENTION

Figure 1:
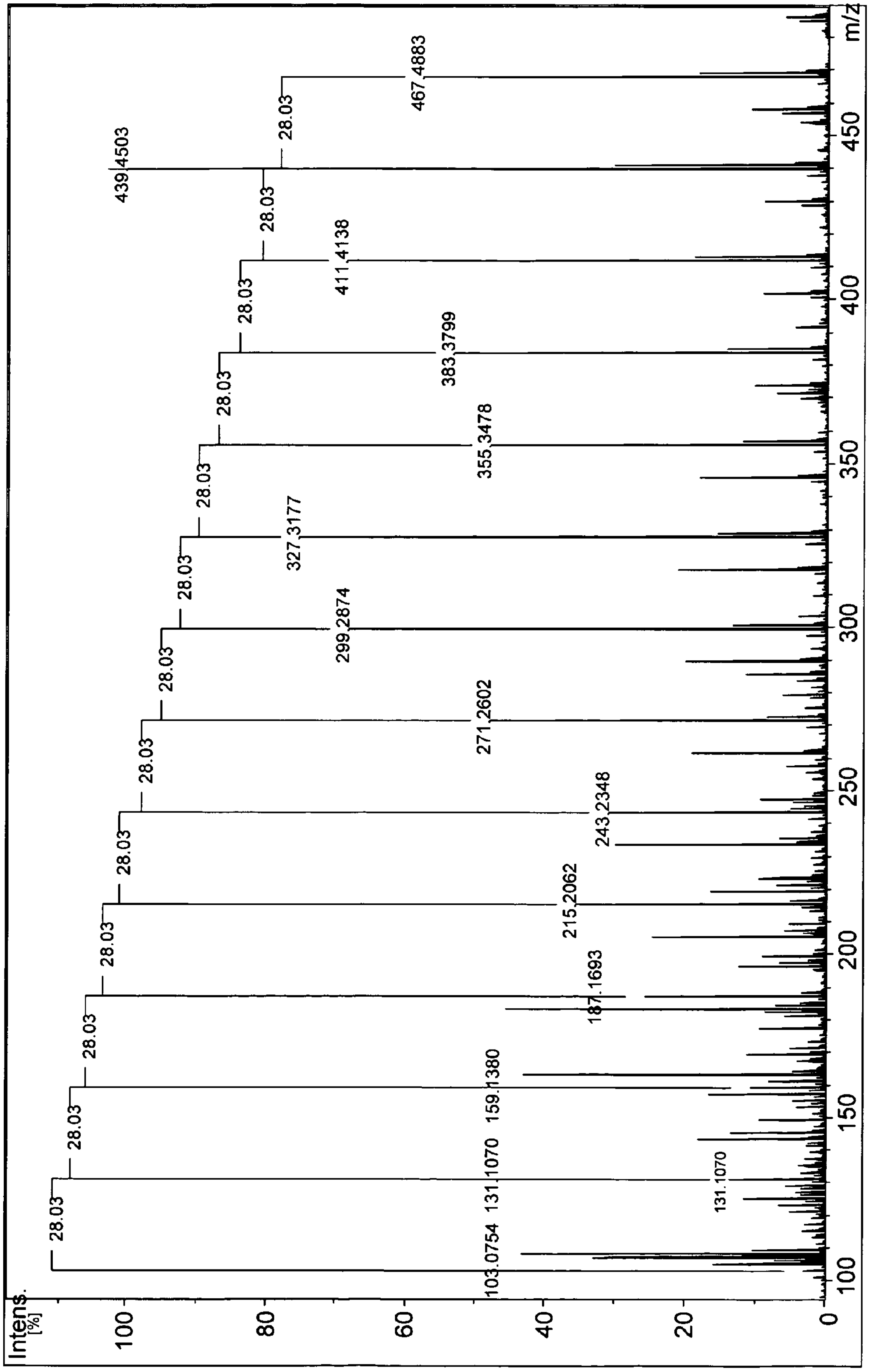
FIGS. 1 and 2 illustrate the APCI mass spectra of the proposed mixture of odd-numbered saturated fatty acids in the positive and negative acquisition modes respectively.

An aspect of the present invention provides, particularly for APCI but also for APPI, a mixture of fatty acids in specified concentrations, which are preferably dissolved in toluene and yield sufficient reference masses in the low-mass range from 100 daltons to 500 daltons for calibration of the mass scale.

The fatty acids in the mixture preferably comprise a continuous series of saturated, unbranched, odd-numbered fatty acids extending from 5 C-atoms (valeric acid) up to 31 C-atoms, to yield 14 reference points. These odd-numbered fatty acids scarcely occur in plants, and are only rarely found in animal fats (e.g., 5 percent, at most). They have slightly lower melting and boiling points in comparison to the even-numbered fatty acids, if the mean value of two neighboring fatty acids of the complete series are compared, which is advantageous for vaporization. They are thermally stable when vaporized. Preferably the difference in mass between the odd-numbered fatty acids is 28 daltons in each case; more precise values can be found in the appropriate tables of atomic weights. Control and analysis software in commercially available mass spectrometers contains stored data and executable program instructions for calculating the masses.

In the positive operating mode, the protonated fatty acid molecule ions are measured, while the deprotonated ions are measured in the negative mode. The fatty acids are nontoxic. They are preferably dissolved in toluene for use, and the toluene serves as an aromatic mediator for ionizing the fatty acids for APPI. Because toluene is not suited as a mediator for the CI ionization of all fatty acids in the series, some chloroform can be added as a second mediator. A preferred mixture of the continuous series of saturated, odd-numbered fatty acids from C5 to C31 yields 14 reference points, extending from about 103 to 467 daltons in the positive mode, and about 14 reference points extending from 101 to 465 daltons in negative mode.

Figure 3:
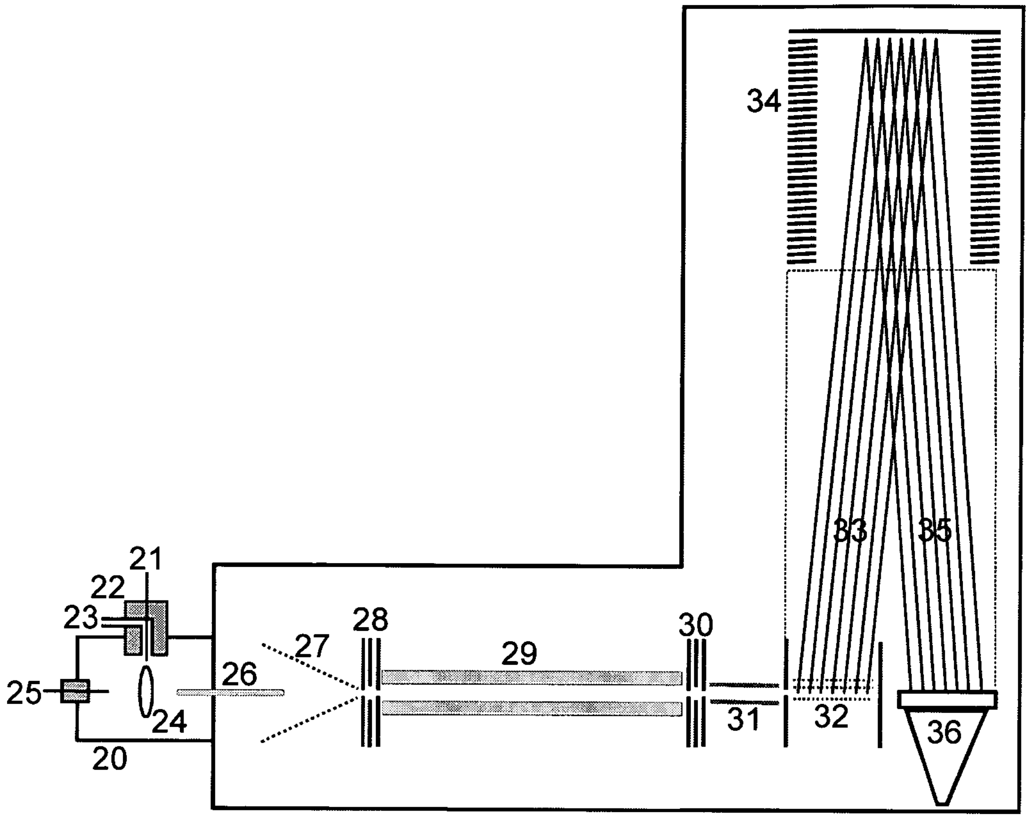
FIG. 3 is a block diagram illustration of a reflector time-of-flight mass spectrometer with orthogonal ion injection (OTOF) that is equipped with an APCI ion source.

FIG. 3 is a block diagram illustration of a time-of-flight mass spectrometer. In an ion source 20, which has a spray capillary 21 in a heating block 22 with a spray gas feed 23, analyte ions 24 are generated at atmospheric pressure by chemical ionization via primary ions from a corona discharge at the metal tip 25. The analyte ions 24 are introduced into the vacuum system through a capillary 26. An ion funnel 27 collects the ions and guides them through a lens system 28 into an ion guide system 29, from where ions are formed into a fine beam of ions by a further lens system 30. The pulser 32 is supplied with the ions from this fine primary beam. Between the lens system 30 and the pulser 32, the flight path is screened by a casing 31 in order to reduce the electrical influence of the lens system 30 and the pulser 32 on each other and, particularly, to reduce electrical and magnetic interference on the primary ion beam. The pulser 32 pulses out a section of the primary ion beam orthogonally, so creating a secondary ion beam 33. This ion beam 33 is reflected in the reflector 34 with velocity focusing and measured with high time resolution in the detector 36.

Figure 4:
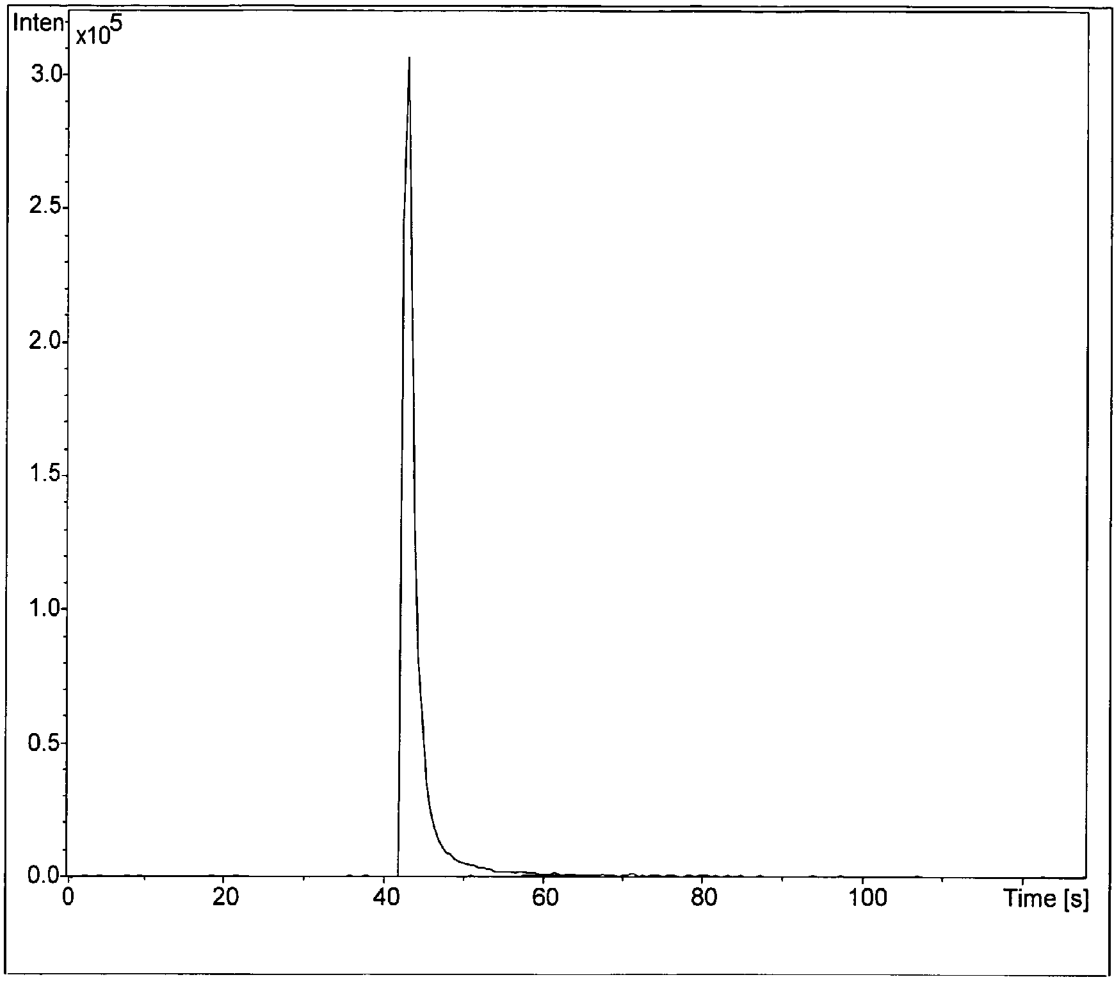
FIG. 4 illustrates a plot of the ion intensities versus time after APCI ionization of the calibration mixture, showing that the ion signals have attenuated after about 30 seconds to the degree that analytical operation can recommence.

Referring to FIG. 3, the solution of fatty acids in toluene is preferably injected into the heating block 22 for the spray gas, for example via the inlet 23 for the spray gas. The heating block should be set to a temperature of at least about 350° C., but preferably 375° C. or even higher. Between one and two microliters of solution are enough to acquire mass spectra for a period of several seconds. Since OTOF mass spectrometers work with an acquisition rate of between about 5000 and 10,000 individual mass spectra per second, which are added together to form a sum spectrum, a good mass spectrum for calibration is obtained within a few seconds. As can be seen in FIG. 4, the signals from the calibration substances fade after only about 30 seconds to a level at which analytical operation can start again, for instance with a new chromatographic run. It is contemplated that calibration may be performed in the middle of longer chromatographic runs.

Although a solvent that includes toluene with additional chloroform acting as mediators does also allow the non-aromatic fatty acids in the proposed mixture to be reasonably well ionized by APPI and APLI, a mixture of aromatically modified fatty acids (phenyl or naphthyl fatty acids) may be used for APPI and APLI. This yields an improved reference mass spectrum because the aromatic groups permit direct absorption of UV radiation, and therefore direct ionization. The phenyl and naphthyl fatty acids are also nontoxic. Here again, the odd-numbered, unbranched, saturated fatty acids are preferred.

Figure 2:
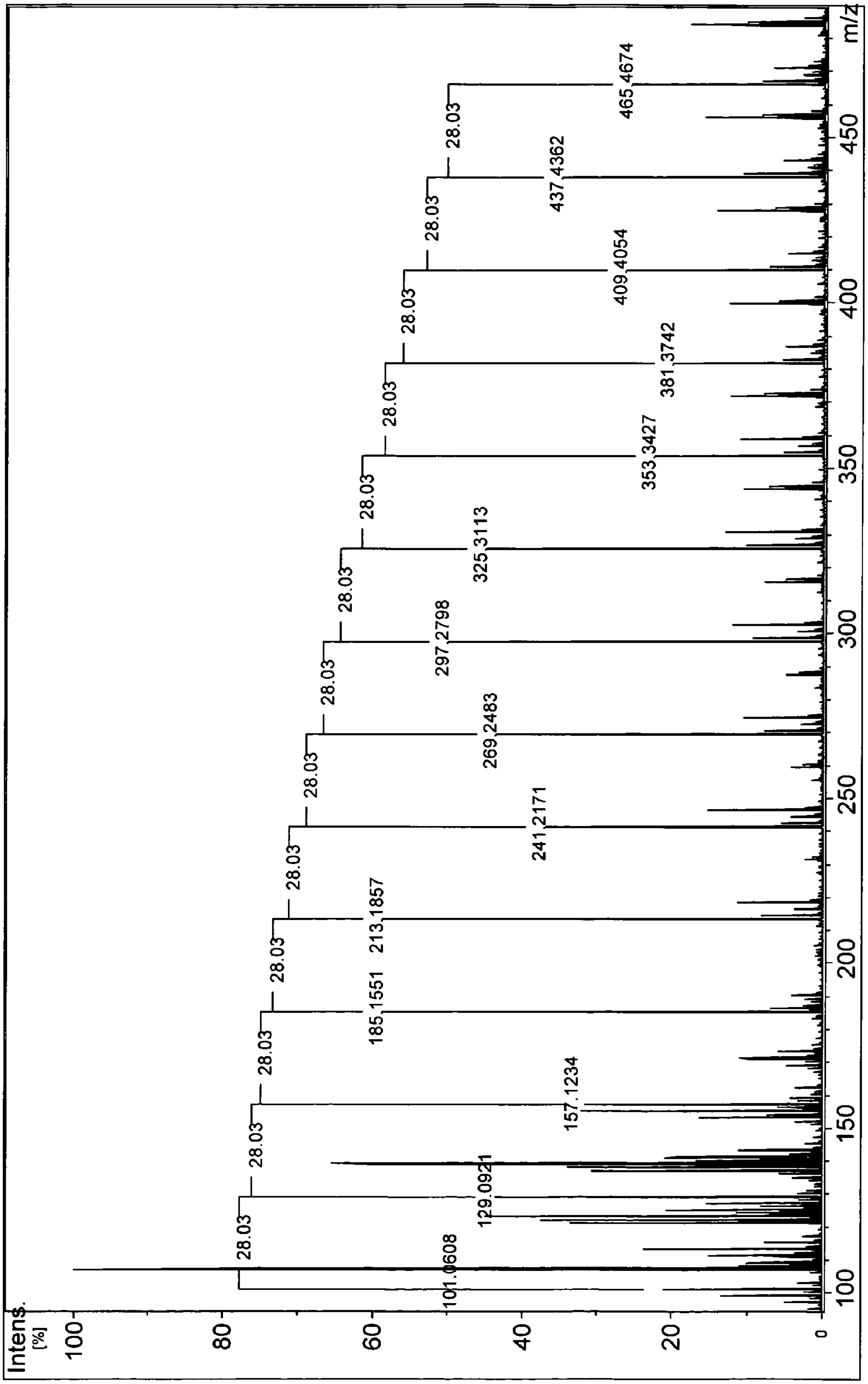

FIGS. 1 and 2 illustrate the positive and negative APCI mass spectra of the preferred mixture of saturated, odd-numbered fatty acids from C5 to C31. The ion signals between the 14 reference points largely originate from the toluene in various states of hydroxylation, and from complex ions including fatty acids with toluene. Both mass spectra are ideal for mass scaling. Uneven signal heights from the fatty acids can be compensated for by modifying the concentrations.

The demand for a mixture of calibration substances that cover the lower mass range up to 500 daltons originates in the deviations, only recently researched, of the calibration curve from the ideal function, $m/z=a\times t^2$, which necessarily occur in practically any time-of-flight mass spectrometer that operates with pulsed acceleration. This effect also occurs in time-of-flight mass spectrometers with orthogonal ion injection, since the ions are subjected to an acceleration that is suddenly switched on.

The problem, discussed above, of the distortion of the calibration curve in the lower mass range occurs as a result of the voltages at the acceleration diaphragms in the pulser 32 being switched. The acceleration voltage only approaches the desired final value with a time constant of a few nanoseconds. The critical damping condition for the transient is particularly advantageous but difficult to establish, and it cannot always be maintained during operation. Periodic overshooting of the accelerating voltage should be avoided as far as possible when switching, as otherwise the overshooting oscillations will have a dramatically distorting effect on the calibration curve, making calibration even more difficult. It is, however, not always possible to completely avoid these overshootings because usually not just one voltage has to be switched, but several voltages at different pulser electrodes simultaneously.

The determination of the mass to an accuracy better than a hundred-thousandth of the total mass, preferably even of a millionth, is particularly required for the calculation of the molecular formulae of the substances being investigated. This problem is familiar to those skilled in the art.

Especially when gas chromatography is coupled with time-of-flight mass spectrometers of high mass accuracy, it is crucial to produce unambiguous molecular formulae for the analyte molecules. Up to now, gas chromatography has usually been coupled with ion trap or quadrupole mass spectrometers via electron impact (EI) ion sources. The lower mass accuracy of such combinations means that substances can only be identified by spectral comparisons of the signal-rich EI mass spectra, failing only in the case of unknown substances, for instance in the analysis of unknown natural products. But for coupling GC with APCI or APPI sources, only molecular ions are formed, and the determination of the molecular formula is crucial for any substance identification.

A "calibration curve" is, in principle, an equation that describes the relationship between the mass and the flight time. But the term "calibration curve" is also applied to equations which are approximations only. The calibration curve contains a series of coefficients that can be determined by comparing known masses of the ions of calibration substances with their measured flight times by an adaptation program (usually by minimizing the squared deviations).

The proposed mixtures of fatty acids in solution may be used for either manual or automated calibration procedures. In either case the solution may be injected into the heating block 22 (FIG. 3), preferably in the inlet 23 (FIG. 3) for the spray gas. The injection can be effected by a manual or motor-driven syringe. Because the needle of the syringe is located in the spray gas, which is still cool, hardly any additional solvent is delivered after the injection; nevertheless, it is advantageous to withdraw the syringe needle after the injection, or at least to draw back the solvent that is in the syringe needle. Automatic calibration requires a motor-operated syringe to be installed; this can in most cases be controlled by the executable program instructions of the control software, as is known to those skilled in the art.

Although the present invention has been illustrated and described with respect to several preferred embodiments thereof, various changes, omissions and additions to the form and detail thereof, may be made therein, without departing from the spirit and scope of the invention.

What is claimed is:

1. A calibration substance mixture for the mass calibration in a mass range below 500 daltons, for time-of-flight mass spectrometers comprising APCI or APPI ion sources, comprising a series of at least five odd-numbered saturated fatty acids (alkane carboxylic acids), starting from Valeric acid (C5), in a solvent, wherein the solvent comprises a mixture of toluene and chloroform.

2. A calibration substance mixture for the mass calibration of time-of-flight mass spectrometers comprising APPI or APLI ion sources, in the mass range below 500 daltons, comprising at least five phenyl fatty acids or naphthyl fatty acids in a solvent.

3. The calibration substance mixture of claim 2, wherein the phenyl or naphthyl fatty acids are dissolved in toluene.

4. A method of mass calibrating a mass spectrometer in a mass range below 500 Daltons, comprising:

(a) injecting a calibration substance mixture that includes at least five fatty acids in a solvent into a heating block of the mass spectrometer;

(b) forming ions from the calibration substance mixture using an atmospheric pressure ion source, wherein both aromatic and non-aromatic substances are used as mediator substances for the ionization of the fatty acids;

(c) measuring time-of-flight mass spectra of the ions;

(d) determining coefficients of a calibration curve by comparing known masses of the ions of the calibration substance mixture with their measured flight times using an adaptation algorithm; and (e) calibrating a mass scale of the time-of-flight mass spectra using the calibration curve .

5. The method of claim 4, wherein the fatty acids comprise a series of odd-numbered saturated fatty acids.

6. The method of claim 5, wherein the series of odd-numbered saturated fatty acids starts at Valeric acid (C5).

7. The method of claim 4, wherein the atmospheric pressure ion source is one of APCI, APPI, and APLI ion source.

8. The method of claim 4, executed in an automated manner prior to or during analytical measurement runs for compensating for a drifting of the mass scale.

9. A method of mass calibrating a mass spectrometer in a mass range below 500 Daltons, comprising:

(a) injecting a calibration substance mixture that includes at least five fatty acids in a solvent, which comprises a mixture of toluene and chloroform, into a heating block of the mass spectrometer;

(b) forming ions from the calibration substance mixture using an atmospheric pressure ion source;

(c) measuring time-of-flight mass spectra of the ions;

(d) determining coefficients of a calibration curve by comparing known masses of the ions of the calibration substance mixture with their measured flight times using an adaptation algorithm; and (e) calibrating a mass scale of the time-of-flight mass spectra using the calibration curve.

10. A method of mass calibrating a mass spectrometer in a mass range below 500 Daltons, comprising:

(a) injecting a calibration substance mixture that includes at least five fatty acids, which comprise phenyl fatty acids or naphthyl fatty acids, in a solvent into a heating block of the mass spectrometer;

(b) forming ions from the calibration substance mixture using an APPI or APLI atmospheric pressure ion source;

(c) measuring time-of-flight mass spectra of the ions;

(d) determining coefficients of a calibration curve by comparing known masses of the ions of the calibration substance mixture with their measured flight times using an adaptation algorithm; and (e) calibrating a mass scale of the time-of-flight mass spectra using the calibration curve.

11. The method of claim 10, wherein the phenyl or naphthyl fatty acids are dissolved in toluene.

12. A calibration substance mixture for the mass calibration of mass spectrometers comprising APPI or APLI ion sources, in the mass range below 500 daltons, comprising a total number of at least five fatty acids, the fatty acids comprising phenyl fatty acids, naphthyl fatty acids or a mixture thereof, in a solvent.

13. A calibration substance mixture for the mass calibration in a mass range below 500 daltons, for time-of-flight mass spectrometers comprising APCI or APPI ion sources, comprising a series of at least five odd-numbered saturated fatty acids (alkane carboxylic acids), starting from Valeric acid (C5), in a solvent, wherein the solvent comprises a mixture of an aromatic mediator substance and a non-aromatic mediator substance.

14. A method of mass calibrating a mass spectrometer in a mass range below 500 Daltons, comprising:

injecting a mixture of calibration substance capable of framing both positive ions and negative ions in a solvent into a heating block of the mass spectrometer, wherein the calibration substances are at least five saturated odd-numbered fatty acids taken from the range of 5 C-atoms (Valeric acid) to 31 C-atoms;

providing an atmospheric pressure ion source that is configured and arranged to selectively operated in one of a positive mode and a negative mode;

forming ions in one of the positive mode and negative mode from the calibration substance mixture using the atmospheric pressure ion source;

measuring time-of-flight mass spectra of the ions;

determining coefficients of a calibration curve by comparing known masses of the ions of the calibration substance mixture with their measured flight times using an adaptation algorithm; and calibrating a mass scale of the time-of-flight mass spectra using the calibration curve.

* * * * *

UNITED STATES PATENT AND TRADEMARK OFFICE

CERTIFICATE OF CORRECTION

PATENT NO. : 8,563,315 B2
APPLICATION NO. : 12/727829
DATED : October 22, 2013
INVENTOR(S) : Zey et al.

It is certified that error appears in the above-identified patent and that said Letters Patent is hereby corrected as shown below:

In the Claims

Column 9
Line 18, please delete “framing” and insert -- forming --

Signed and Sealed this
Tenth Day of December, 2013

Margaret A. Focarino
*Commissioner for Patents of the United States Patent and Trademark Office*